United States Patent [19]

Ito et al.

[11] Patent Number: 5,128,478

[45] Date of Patent: Jul. 7, 1992

[54] OXAZOLINE-CARBOXYLIC ACID DERIVATIVES AND METHOD FOR THE PREPARATION THEREOF

[75] Inventors: Yoshihiko Ito; Tamio Hayashi, both of Kyoto, Japan

[73] Assignee: Ajinomoto Co., Inc., Tokyo, Japan

[21] Appl. No.: 565,208

[22] Filed: Aug. 9, 1990

Related U.S. Application Data

[60] Division of Ser. No. 266,327, Nov. 1, 1988, abandoned, which is a continuation of Ser. No. 71,030, Jul. 8, 1987, abandoned.

[30] Foreign Application Priority Data

Sep. 2, 1986 [JP] Japan .................. 61-206234

[51] Int. Cl.⁵ .......................................... C07D 236/08
[52] U.S. Cl. .................................................. 548/237
[58] Field of Search .................... 548/237; 514/374

[56] References Cited

U.S. PATENT DOCUMENTS

| | | | |
|---|---|---|---|
| 2,562,113 | 7/1951 | Moersch | 548/237 |
| 2,768,972 | 10/1956 | Tchoubar | 548/237 |
| 4,026,901 | 5/1977 | Coffen | 548/236 |
| 4,588,694 | 5/1986 | Hamaguchi | 548/229 |

FOREIGN PATENT DOCUMENTS

| | | |
|---|---|---|
| 2558158 | 7/1976 | Fed. Rep. of Germany . |
| 728704 | 4/1955 | United Kingdom ............... 548/237 |
| 0728708 | 4/1955 | United Kingdom . |

OTHER PUBLICATIONS

Miyoshi (II), CA: 84: 17729b, May 1975.
Ito, CA: 107: 236569w, v28, 1986.
Miyoshi, Chem. Abstr. vol. 84, No. 17729b, May, 1975.
Ito, Y. (1986) Tennen uki Kagobutou Toronkai Koen Yoshishu, 28th, pp. 520-525 (Chem. Abs. 107: 236569w).
Heinzer, F. (1981) Helv. Chim. Acta., 64(7), pp. 2279-2297 (Chem. Abs. 96: 104711f).
Schoellkopf, U. (1981) Leibig's Ann. Chem., 8, pp. 1469-1475 (Chem. Abs. 95: 204386b).
JP 50-52025; May 1975; Miyoshi, M. (Chem. Abs. 84: 17729b).
Matsumoto, K. (1975) Agric. Biol. Chem. 39(9), pp. 1869-1873 (Chem. Abs. 83: 179551u).
Hoppe, D. (1972) Liebigs Ann. Chem., 763, pp. 1-16 (Chem. Abs. 78: 71964p).

*Primary Examiner*—Johnnie R. Brown
*Assistant Examiner*—Frederick F. Tsung
*Attorney, Agent, or Firm*—Oblon, Spivak, McClelland, Maier & Neustadt

[57] ABSTRACT

Optically active oxazoline-carboxylic acid derivatives of the formula:

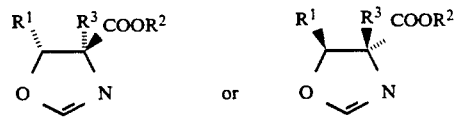

wherein $R^1$ represents a hydrogen atom, an alkyl group having 1 to 20 carbon atoms, an alkykl group which is substituted and has 1 to 20 carbon atoms, a cycloalkyl group, a cycloalkyl group which is substituted, a phenyl group, a phenyl group which is substituted, a vinyl group, a vinyl group which is substituted, an ethynyl group or an ethynyl group which is substituted;

$R^2$ represents a lower alkyl group having 1 to 4 carbon atoms or a benzyl group;

$R^3$ represents a hydrogen atom, a lower alkyl group having 1 to 4 carbon atoms, a phenyl group or a benzyl group, and a method for preparing the above compounds and derivatives thereof involving a reaction between an aldehyde and an isocyano-carboxylate in the presence of a catalyst mixture.

5 Claims, No Drawings

OXAZOLINE-CARBOXYLIC ACID DERIVATIVES AND METHOD FOR THE PREPARATION THEREOF

This application is a Division of application Ser. No. 07/266,327 filed on Nov. 1, 1988, now abandoned, which was a continuation of Ser. No. 07/071,030, filed on Jul. 8, 1987, now abandoned.

BACKGROUND OF THE INVENTION

1. Field of the Invention

The present invention relates to new optically active oxazoline-carboxylic acid derivatives, specifically optically active trans-2-oxazoline-4-carboxylate derivatives, which can be used in the preparation of optically active amino acids such as threonine, dihydroxyphenylserine and the like, and to a method for preparing the said derivatives.

2. Description of the Prior Art

There are many optically active β-hydroxy-α-amino acids having important physiological activity. For example, the L-form of threonine, having the threo configuration and having the following formula:

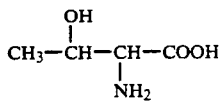

is an essential amino acid, which cannot be formed in vivo in animals by biosynthesis.

In addition, an L-threo-3-(3,4-dihydroxyphenyl) serine of the following formula:

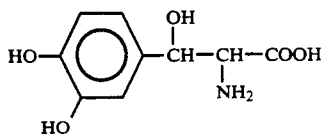

is known to be useful as a remedy for peripheral orthostatic hypotension (Japanese Patent Application OPI No. 104815/81), a remedy for Parkinson's disease (Japanese Patent Application OPI No. 52219/83) or a diuretic (Japanese Patent Application OPI No. 85318/86). (The term "OPI" is used herein means an unexamined and published application.)

When the above optically active β-hydroxy-α-amino acids have a substituent in the β position, there are two possible configurations, the threo-form and the erythro-form, and each of these forms include the respective optical isomers. Accordingly, for example, when an L-threo form is to be obtained, it must be obtained from a mixture comprising at least four kinds of stereoisomers. In a previous purification scheme, the erythro form is first removed from the mixture and then the L-threo form is obtained by optical resolution. In the case where the D-form is required, it is prepared in the same manner. This conventional means is, however, defective in that the operation is complicated and the yield is poor.

On the other hand the reaction of an aldehyde and an isocyano-carboxylate has been known to proceed in the presence of an amine such as triethylamine, as follows:

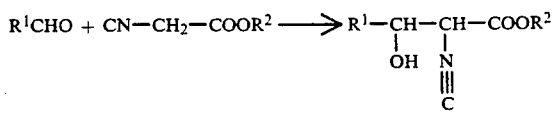

Further, compound II above is known to cyclize in the presence of a metal to give a 2-oxazoline-4-carboxylate derivative as follows:

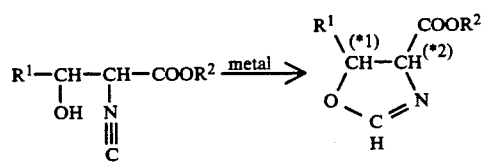

In the above formula the selectivity of forming the D- or L-form in the *1- and *2-positions in the 2-oxazoline-4-carboxylate derivative has not yet been reported.

The above-described conventional chemical synthesis of optically active threo-β-hydroxy-α-amino acids requires complicated operations which include the separation of the products on the basis of a difference in configuration, followed by successive separation of the optically active isomers. This is because the direct asymmetric synthesis of the desired chemical substance is impossible.

In view of the prior art methods described above, it can be seen that a need continues to exist for a method for preparing a desired optically active amino acid such as an optically active β-hydroxy-α-amino acid, which is both simple and which results in a higher yield as compared to the known conventional methods. There is also a need to provide new starting materials for the preparation of desired final products, such as optically active amino acids.

SUMMARY OF THE INVENTION

Accordingly, it is an object of the present invention to provide a method for preparing optically active oxazoline-carboxylic acid derivatives;

It is also an object of the present invention to provide optically active oxazoline-carboxylic acid derivatives;

It is yet another object of the present invention to provide a method for preparing optically active threo-β-hydroxy-α-amino acids.

According to the present invention, the foregoing and other objects have been attained by a process whereby new optically active trans-2-oxazoline-4-carboxylate derivatives are prepared from an aldehyde and an isocyano-carboxylate by the method hereinbelow described. The present invention has also established a method for preparation of the desired optically active threo-β-hydroxy-α-amino acids from the said optically active trans-2-oxazoline-4-carboxylate derivatives.

DETAILED DESCRIPTION OF THE PREFERRED EMBODIMENTS

As a result of their studies, the present inventors have discovered that optically active oxazoline-carboxylic acid derivatives of the following general formulas:

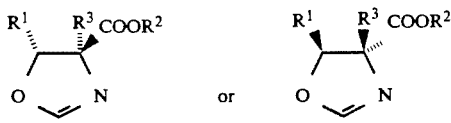

may be prepared by reacting an aldehyde of a general formula:

$R^1CHO$ in which $R^1$ represents a hydrogen atom, an alkyl group having 1 to 20 carbon atoms, an alkyl group which is substituted and has 1 to 20 carbon atoms, a cycloalkyl group, a cycloalkyl group which is substituted, a phenyl group, a phenyl group which is substituted, a vinyl group a vinyl group which is substituted, an ethynyl group or an ethynyl group which is substituted, and an isocyano-carboxylate of a general formula:

in which $R^2$ represents a lower alkyl group having 1 to 4 carbon atoms or a benzyl group; $R^3$ represents a hydrogen atom, a lower alkyl group having 1 to 4 carbon atoms, a phenyl group or a benzyl group, in the presence of a catalyst.

Further, they have developed a direct preparation of optically active threo-β-hydroxy-α-amino acids which involves hydrolyzing and said optically active oxazoline-carboxylic acid derivative.

The overall reaction scheme of the present invention is represented by the following:

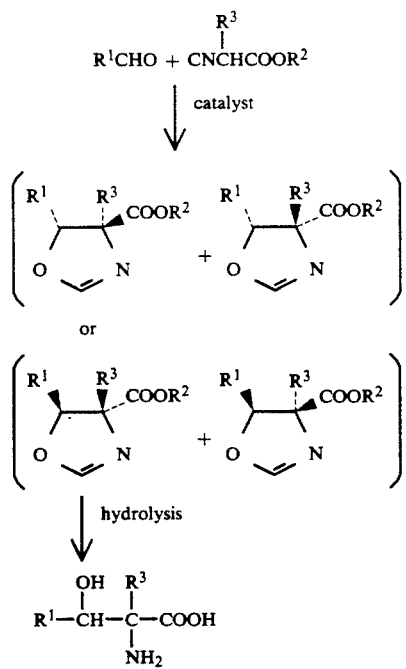

The catalyst to be used in the reaction of the aldehyde and the isocyano-carboxylate is a complex formed by the reaction of a IB-group metal (or metal-containing compound) and a ferocene face-asymmetric and optically active N-methyl-N-[2-(disubstituted amino)ethyl or 3-(disubstituted amino)propyl]-1-[1',2-bis (diphenylphosphino)-ferrocenyl]ethylamine of a general formula:

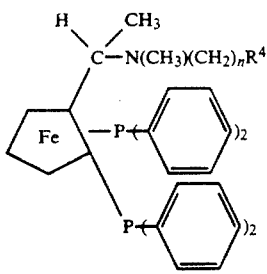

or

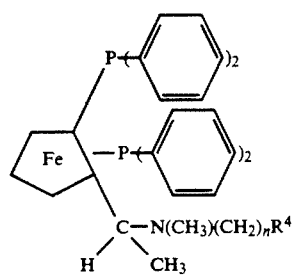

in which $R^4$ represents a substituted amino group such as a dimethylamino group, a diethylamino group, a morpholino group, a piperidino group or an N-methylpiperazino group; and n represents 2 to 3.

As the IB-group metal-containing compound, for example, a bis(cyclohexylisocyanide)-M tetrafluoroborate of the following general formula:

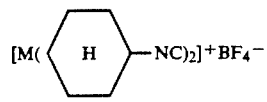

in which M represents gold or silver, AuCl or AgO-SO$_2$CF$_3$ are preferably used. The said compounds are exemplary only and any other IB-group metal compounds can be used in the present invention. On the other hand, an optically active (R)-N-methyl-N-[2-(disubstituted amino)ethyl or 3-(disubstituted amino)propyl]-1-[(S)-1',2-bis(diphenylphosphino-ferrocenyl)]-ethylamine or an optically active (S)-N-methyl-N-[2-(disubstituted amino)ethyl or 3-(disubstituted amino)propyl]-1-[(R)-1',2-bis(diphenylphosphino)ferrocenyl]-ethylamine can be used, for instance, as the ferrocene face-asymmetric and optically active N-methyl-N-[2-(disubstituted amino)ethyl or 3-(disubstituted amino)-propyl]-1-[1',2-bis (diphenylphosphino)ferrocenyl]-ethylamine.

From among the above-mentioned ferrocene derivatives, an L-amino acid or a D-amino acid can selectively be obtained by the selective use of the former and the latter compounds.

As the di-substituted amino group, there can be used a dimethylamino group, a diethylamino group, a morpholino group, a piperidino group, an N-methylpiperazino group or the like.

Bis(cyclohexylisocyanide)-gold tetrafluoroborate can be prepared in accordance with the description as given in *Gazz. Chim. Ital.*, Vol. 103, page 373, 1973; and ferrocene face-asymmetric and optically active N-methyl-N-[2-(disubstituted amino)ethyl or 3(disubstituted amino)-propyl]-1-[1',2-bis(diphenylphosphino)ferrocenyl]-ethylamines in *Bull. Chem. Soc. Jpn.*, Vol. 53, page 1138, 1980. However, when the components are used singly as a catalyst, preparation of the optically active oxazoline-carboxylates from the aldehyde and the isocyano-carboxylate, which is the object of the present invention, is impossible. Only by the combined use of the two components, can the optically active oxazoline-carboxylic acid derivatives, more precisely the optically active trans-2-oxazoline-4-carboxylate derivatives, be obtained from the aldehyde and the isocyano-carboxylate. The amount of the catalyst to be used is 0.01% or more as a molar ratio to the substrates. Preferably 0.01% to 1% as a molar ratio may be employed, particularly preferably 0.01 to 0.10%.

The group $R^1$ in the aldehyde of formula $R^1CHO$ to be reacted is not specifically limited. In general, the group $R^1$ may be an alkyl group having from 1 to 20 carbon atoms, such as methyl, ethyl, propyl, isopropyl, butyl, sec-butyl, t-butyl, dodecanyl or octadecanyl; an alkyl group which is substituted and has 1 to 20 carbon atoms; a cycloalkyl group such as cyclopentyl or cyclohexyl; a cycloalkyl group which is substituted; a phenyl group; a phenyl group which is substituted; a vinyl group; a vinyl group which is substituted; an ethynyl group or an ethynyl group which is substituted.

As used herein, "substituted" means that a group may have attached thereto a halogen (i.e. Cl, Br, F, I), a lower ($C_1$–$C_6$) straight chain, branched or cyclic alkyl or alkoxyl, hydroxy, amino, $C_1$–$C_6$ alkyl- or dialkyl-amino, $C_1$–$C_6$ acyl, phenyl, or other similar moieties. "Substituted" also encompasses more than one attached substituent, such as, for example, 2-5.

The group $R^2$ in the isocyano-carboxylate of formula

which is the other reaction substrate besides the aldehyde is also not specifically limited. In general, the group $R^2$ is a lower alkyl group having 1 to 4 carbon atoms, such as methyl, ethyl, propyl, isopropyl, butyl, sec-butyl or t-butyl; or a benzyl group.

As $R^3$, any one of a hydrogen atom, a lower alkyl group having 1 to 4 carbon atoms, a phenyl group or a benzyl group may be used.

Regarding the solvent to be used in the reaction, there may be used halogenated hydrocarbons such as chloroform, dichloromethane or ethylene dichloride; ether-type solvents such as tetrahydrofuran or diethylether; aromatic hydrocarbons such as benzene or toluene; and esters such as ethyl acetate.

Regarding the reaction conditions, the reaction temperature is suitably 5° to 100° C., preferably 20° to 50° C.; and the reaction time is suitably 10 to 50 hours, preferably 20 to 40 hours. The reaction yield is almost quantitative.

The optically active oxazoline-carboxylic acid derivatives thus obtained include trans-forms and cis-forms.

Specifically, the derivatives include optically active trans-2-oxazoline-4-carboxylate derivatives of the general formula:

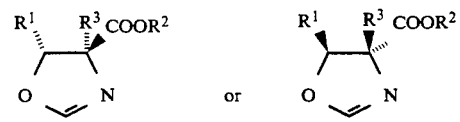

and optically active cis-2-oxazoline-4-carboxylate derivatives of the general formula:

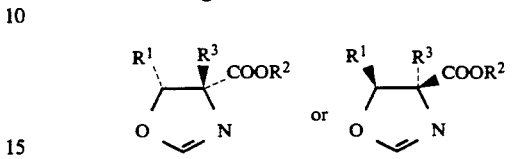

In the product as formed, the ratio of the transform to the cis-form is generally 80–100 : 20–0, which means that the proportion of the trans-form is predominant in the product.

If necessary, the cis-form and the trans-form can easily be separated from each other by means of column chromatography with a silica-gel.

The optical purity of the trans-2-oxazoline-4-carboxylic acid derivative is 80% ee (enantiomeric excess) or more, and in a preferred case, a product having an optical purity of 97% ee or more can be obtained.

The optically active trans-2-oxazoline-4carboxylate derivatives thus obtained can be used in the preparation of optically active threo-β-hydroxy-α-amino acids having physiological activity, through the hydrolysis of the said derivatives. For examples, there may be mentioned L-threonine, which is an essential amino acid, or L-threo-3-(3,4-dihydroxyphenyl)serine, which is a remedy for Parkinson's disease. In addition, these can be used in the synthesis of other D-forms such as D-threonine.

The hydrolysis reaction can be carried out by the method as described in *Agric. Biol. Chem.*, Vol. 42, page 1565, 1978. Specifically, the optically active carboxylate derivative is heated in 1N to 12N HCl at 40° to 100° C. for 3 to 12 hours, successively treated with Amberlite IR-120B and thereafter recrystallized to give an optically active threo-form β-hydroxy-α-amino acid.

Alternatively, the said derivative is heated in an alcohol solvent in the presence of a concentrated hydrochloric acid solution in the same manner as above to give an optically active threo-type β-hydroxy-α-amino acid ester.

By the use of a catalyst comprising a combination of a metal compound such as bis(cyclohexylisocyanide)-gold or silver tetrafluoroborate, AuCl or $AgOSO_2CF_3$, and a ferrocene face-asymmetric and optically active N-methyl-N-[2-(di-substituted amino)ethyl or 3-(disubstituted amino)propyl]-1-[1',2-bis(diphenylphosphino)-ferrocenyl]ethylamine, an optically active oxazoline-carboxylic acid derivative, more precisely an L-form or D-form optically active trans-2-oxazoline-4-carboxylate ester derivative, can be obtained from an aldehyde and an isocyano-carboxylate, which has heretofore been considered impossible.

The optically active oxazoline-carboxylic acid derivatives thus obtained can be used as raw materials for the preparation of optically active threo-β-hydroxy-α-amino acids having physiological activity. Specifically, the said optically active oxazoline-carboxylic acid derivatives can be hydrolyzed to give optically active threo-β-hydroxy-α-amino acids.

The process of the present invention for the direct preparation of optically active β-hydroxy-α-amino acids from an aldehyde and an isocyano-carboxylate does not require the separation of the stereoisomeric threo- and erythro-forms, or the separation of the optical isomers of the L-form and the D-form, and is therefore different from any other conventional synthetic means. Thus, the process of the present invention has various merits in that the operation is simple and easy and the yield of the product is high.

The invention now being generally described, the same will be better understood by reference to certain specific examples which are included herein for purposes of illustration only and are not intended to be limiting of the invention or any embodiment thereof, unless specified.

EXAMPLES EXAMPLE 1

27.5 mg (0.055 mmol) of bis(cyclohexylisocyanide)-gold tetrafluoroborate, 39.7 mg (0.056 mmol) of (R)-N-methyl-N-[2-(diethylamino)-ethyl]-1-[(S)-1',2bis( -ethyl-amine and 0.549 g (5.54 mmol) of methyl isocyano-acetate were dissolved in 5.5 ml of dry dichloromethane, and 0.642 g (6.05 mmol) of benzaldehyde was added thereto. The reaction mixture was reacted for 20 hours at 25° C in $N_2$ atmosphere. After the solvent was concentrated, the residue formed was subjected to silica-gel column chromatography (solvent: hexane/ethyl acetate =½) to obtain 0.96 mg (84.6%) of trans-4-methoxycarbonyl-5-phenyl-2-oxazoline and 0.12 g (10.4%) of the corresponding cis-form.

The NMR-spectrum, optical rotation and optical purity of each of the trans-form and cis-form thus obtained were determined.

Trans-form: (4S, 5R)

(1) NMR (CDCl$_2$/TMS) spectrum:
δ: 3.83 (s, 3H)
4.63 (dd, J = 2.2 and 7.9 Hz, 1H)
5.70 (d, J = 7.9 Hz, 1H)
7.11 (d, J = 2.2 Hz, 1H)
7.30–7.42 (m, 5H).

(2) Optical rotation:
$^{20}_D$ +297°(c=1.2 THF)

(3) Optical purity:
The optical purity was 96% ee, when measured by the use of tris-[d,d-dicamphoryl methanate]europium-(III) [Eu(dcm)$_3$]

Cis form: (4R 5R)

(1) NMR (CDCl$_2$/TMS) spectrum:
δ: 3.20 (s, 3H)
5.09 (dd, J = 2.2 and 11.2 Hz, 1 H)
5.74 (d, J = 11.2 Hz, 1 H)
7.25 (d, J = 2.2 Hz, 1H)
7.30–7.42 (m, 5H)

(2) Optical rotation:
$^{20}_D$ −80° (c=1.2, THF)

(3) optical purity: 49% ee. (The measurement was same as the case of the trans-form.)

Next, 0.82 g (4.0 mmol) of the trans-form as obtained was dissolved in 10 ml of 6N-HCl and heated at 80° C. for 6 hours. After being concentrated, the residue was dissolved in 5 ml of water and adsorbed onto an ion-exchange resin Amberlite IR-120B (H+type) and then eluted with 5% aqueous ammonia. The fraction containing the desired product was concentrated and the residue was recrystallized from water-ethanol to obtain 0.65 g (90%) of the desired product of L-(-)-threo-β-phenylserine.

The optical rotation of the L-(-)-threo-β-phenylserine was measured, which was $[α]^{20}_D$ −50.020 (c=2.0, 6N HCl).

The data corresponds to the standard value of $[α]^{20}_D$ −50.2+2° (c=2.0, 6N HCl) as given in *Helv. Chim. Acta.*, Vol. 33, page 2111 (1950).

EXAMPLE 2

25.0 mg (0.05 mmol) of bis(cyclohexylisocyanide)-gold tetrafluoroborate, 40.0 mg (0.055 mmol) of (R)-N-methyl-N-[2-(morpholino)ethyl]-1-[(S)-1',2-bis(di-phenylphosphino) ferrocenyl]-ethylamine and 0.567 g (5.72 mmol) of methyl isocyano-acetate were dissolved in 5 ml of methylene chloride, and then, 0.846 g (5.64 mmol) of piperonal was added thereto and stirred for 30 hours at 25° C. After distillation under reduced pressur (135° C./0.3 mmHg), 1.21 g (87%) of 4-carbomethoxy-5-(3,4-methylenedioxyphenyl)-2was obtained. This was subjected to the same column chromatography as in Example 1 to separate it into 96% of the trans-from and 4% of the cis-form.

The optical purity of the trans-form (4S, 5R) was confirmed to be 98% ee by the same NMR analysis as Example 1.

The NMR spectrum (CDCl$_3$/TMS) of the trans-form (4S, 5R) is as follows:
δ: 3.76 (s, 3 H)
4.52 (dd, J = 2 and 8 Hz, 1 H)
5.50 (d, J = 8 Hz, 1H)
5.85 (s, 2H)
6.67 (m, 3H)
6.94 (d, J = 2 Hz, 1H)

EXAMPLE 3

Using various kinds of aldehydes, corresponding oxazoline derivatives were obtained in the same manner as Example 1. The yield, the ratio of the trans-form to the cis-form, the optical purity of the trans-form, the optical rotation and the NMR-spectrum of the oxazoline were measured for each product, and the results are set forth in the following Table 1.

TABLE 1

| $R^1$ in Aldehyde | $R^4$ in Catalyst (n = 2) | Yield (cis/trans) | Ratio in product (cis/trans) | Optical purity of trans-form (ee) | Optical rotaion $[α]_D^{20}$ (THF) | NMR-spectrum |
|---|---|---|---|---|---|---|
| (E)-CH$_3$.CH$_2$CH$_2$CH=CH | N(CH$_3$)$_2$ | 97% | 80/20 | 87(4S, 5R) | +244° | A (see below) |
| (E)-CH$_3$CH=CCH$_3$ | N(CH$_3$)$_2$ | 89% | 91/9 | 95(4S, 5R) | +311° | B (see below) |
| CH$_3$. | 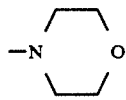 | 88% | 93/7 | 90(4S, 5R) | +216° | |
| (CH$_3$)$_2$CH | N(CH$_2$CH$_3$)$_2$ | 99% | 98/2 | 92(4S, 5R) | +250° | C (see below) |

TABLE 1-continued

| $R^1$ in Aldehyde | $R^4$ in Catalyst (n = 2) | Yield (cis/trans) | Ratio in product (cis/trans) | Optical purity of trans-form (ee) | Optical rotation $[\alpha]_D^{20}$ (THF) | NMR-spectrum |
|---|---|---|---|---|---|---|
|  | $N(CH_2CH_3)_2$ | 95% | 97/3 | 90(4S, 5R) | +236° | |
| | $N(CH_3)_2$ | 96% | 98/2 | 81(4S, 5R) | +202° | D (see below) |
| $(CH_3)_3C$ | $N(CH_2CH_3)_2$ | 100% | 100/0 | 97(4S, 5R) | +265° | E (see below) |

NMR data for each product are set forth as follows:

A: NMR-spectrum
| 0.93 | (t, J = 7 Hz, 3 H) |
| 1.47 | (sextet, J = 7 Hz, 2 H) |
| 2.10 | (q, J = 7 Hz, 2 H) |
| 3.84 | (s, 3 H) |
| 4.44 | (dd, J = 2 and 7.5 Hz, 1 H) |
| 5.15 | (t, J = 7 Hz, 1 H) |
| 5.54 | (dd, J = 7 and 16 Hz, 1 H) |
| 5.96 | (dt, J = 16 and 7 Hz) |
| 7.00 | (d, J = 2 Hz, 1 H). |

B: NMR-spectrum
| 1.58 | (s, 3 H) |
| 1.66 | (d, J = 7 Hz, 3 H) |
| 3.80 | (s, 3 H) |
| 4.41 | (dd, J = 2 and 7.5 Hz, 1 H) |
| 5.07 | (d, J = 7.5 Hz, 1 H) |
| 5.68 | (broad q, J = 7 Hz, 1 H) |
| 6.99 | (d, J = 2 Hz, 1 H). |

C: NMR-spectrum
| 0.96, 0.98 | (a pair of d, J = 7 Hz, 6 H) |
| 1.92 | (octet, J = 7 Hz, 1 H) |
| 3.80 | (s, 3 H) |
| 4.41 | (dd, J = 8 and 2 Hz, 1 H) |
| 4.40–4.65 | (m, 1 H) |
| 6.99 | (d, J = 2 Hz, 1 H). |

D: NMR-spectrum
| 0.7–2.2 | (m, 11 H) |
| 3.80 | (s, 3 H) |
| 4.34–4.64 | (m, 2 H) |
| 6.94 | (d, J = 2 Hz, 1 H). |

E: NMR-spectrum
| 0.92 | (s, 9 H) |
| 3.78 | (s, 3 H) |
| 4.40 | (s, 2 H) |
| 6.95 | (s, 1 H). |

The oxazoline synthesized from $CH_3CHO$ was subjected to column chromatography to isolate the trans-form therefrom, which was hydrolyzed in the same manner as Example 2 and then treated with Amberlite IR-120 and recrystallized from water-methanol, to obtain L-threonine. Yield: 80%.

EXAMPLE 4

39/3 mg (0.55 mmole) of (S)-N-methyl-N-[3-(diethylamino) -propyl]-1-[(R)-1',2-bis(diphenylphosphino)ferrocenyl] -ethylamine and 14.1 mg (0.055 mmole) of silver trifluoromethane-sulfonate was stirred in methylene chloride (5.5 ml) at room temperature for 30 minutes, and then, 0.549 g (5.54 mmole) of methyl isocyano-acetate and 0.642 g (6.05 mmole) of benzaldehyde was added thereto and stirred for 20 hours at 25° C. in nitrogen After being distilled under conditions of 110° C./0.3 mmHg, 1.0 g of 4- methoxycarbonyl-5-phenyl-2-oxazoline (trans/cis =87/13) was obtained. Yield: 91%. The trans-form and the cis-form were separated from each other by column chromatography, and the optical purity of the transform was determined by means of $^1H$ NMR spectroscopy with the same shift reagent $Eu(dcm)_3$ as Example 1, which was 51% ee. After acid-hydrolysis with 6N HCl, L-threo-β-phenylserine, which is a known compound, was obtained.

EXAMPLE 5

Methyl α-methylisocyano-acetate was reacted with benzaldehyde in the presence of the same catalyst and under the same reaction conditions of those of Example 2. After the solvent was concentrated, the reaction mixture was subjected to silica-gel column chromatography to obtain trans-4-methoxycarbonyl-5- phenyl-2-oxazoline and the corresponding cis-form in a ratio of 87/13). Total yield: 90%. The optical purity of the trans-(4S,5R) form was measured in the same manner as in Example 1, which was 93% ee.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method for preparing optically active oxazoline-carboxylic acid derivatives, which comprises:

reacting an aldehyde of the formula:

$$R^1CHO$$

wherein $R^1$ represents a hydrogen atom, an alkyl group having 1 to 20 carbon atoms, an alkyl group which is substituted and has 1 to 20 carbon atoms, a cycloalkyl group, a cycloalkyl group which is substituted, a phenyl group, a phenyl group which is substituted, a vinyl group, a vinyl group which is substituted, an ethynyl group or an ethynyl group which is substituted wherein the substituents which are substituted on each of said alkyl, cycloalkyl, phenyl, vinyl and ethynyl groups are members selected from the group consisting of halogen, lower $C_1$-$C_6$ straight chain, branched or cyclic alkyl or alkoxy, hydroxy, amino, $C_1$-$C_6$ alkyl - or dialkylamino, $C_1$-$C_6$ acyl or phenyl, with a isocyanocarboxylate of the formula:

$$\overset{R^3}{\underset{|}{CNCHCOOR^2}}$$

wherein $R^2$ represents a lower alkyl group having 1 to 4 carbon atoms or a benzyl group;

$R^3$ represents a hydrogen atom, a lower alkyl group having 1 to 4 carbon atoms, a phenyl group or a benzyl group in the presence of a catalyst comprising a IB-group metal and a ferrocene faceasymmetric and optically active N-methyl-N-[2-disubstituted amino) ethyl or 3-(disubstituted amino) propyl]-1-[1',2-bis (diphenylphosphino)ferrocenyl]ethylamine of the formula:

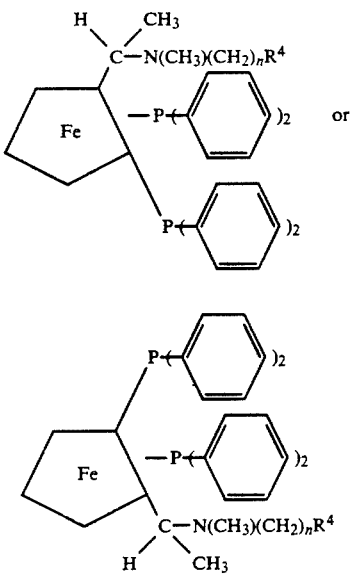

wherein $R^4$ represents a substituted amino group selected from the group consisting of dimethylamino, diethylamino, morpholino, piperidino and n-methylpiperazino; and n is 2 or 3.

2. The process as claimed in claim 1, wherein the IB-group metal is a bis(cyclohexylisocyanide)-M tetrafluoroborate of the following general formula:

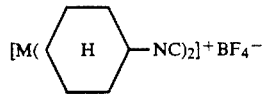

wherein M represents gold or silver; AuCl or AgO-$SO_2CF_3$.

3. The process as claimed in claim 1, wherein the optically active N-methyl-N-[2-(disubstituted amino)ethyl or 3-(disubstituted amino)propyl]-1-[1',2-bis (diphenylphosphino)-ferrocenyl]-ethylamine is an optically active (R)-N-methyl-N-[2-(disubstituted amino)ethyl or 3-(disubstituted amino)propyl]-1-[(S)-1',2-bis (diphenylphosphino)ferrocenyl]-ethylamine or an optically active (S)-N-methyl-N-[2-(disubstituted amino)ethyl or 3-(disubstituted amino)propyl]-1-[(R)-1',2-bis (diphenylphosphino)ferrocenyl]-ethylamine.

4. The process as claimed in claim 1, wherein said reaction is carried out at a temperature of from 5° to 100° C. for from 20 to 40 hours.

5. The process as claimed in claim 1, wherein the amount of said catalyst is 0.01% to 1% as a molar ratio to said aldehyde or said isocyano-carboxylate.

* * * * *

UNITED STATES PATENT AND TRADEMARK OFFICE
CERTIFICATE OF CORRECTION

PATENT NO. : 5,128,478
DATED : July 7, 1992
INVENTOR(S) : ITO et al

It is certified that error appears in the above-indentified patent and that said Letters Patent is hereby corrected as shown below:

| Column | Line | |
|---|---|---|
| 6, | 16, | delete "transform" and insert --trans-form--; |
| 6, | 28, | after "4" insert -- - --; |
| 7, | 17, | delete "EXAMPLES" (first instance); |
| 7, | 21, | delete "2bis(-ethyl-)" and insert -- 2-bis(diphenylphosphino) ferrocenyl]-ethyl--; |
| 7, | 44, | "delete $^{20}_D$ +" and insert --$[\alpha]^{20}_D$--; |
| 8, | 3, | insert --$[\alpha]$-- before "$^{20}_D$ |
| 8, | 17, | delete "50.020" and insert --50.0°; |
| 8, | 31, | delete "pressur" and insert --pressure--; |

UNITED STATES PATENT AND TRADEMARK OFFICE
CERTIFICATE OF CORRECTION

PATENT NO. : 5,128,478

DATED : July 7, 1992

INVENTOR(S) : ITO ET AL

It is certified that error appears in the above-indentified patent and that said Letters Patent is hereby corrected as shown below:

Column    Line

8,    33,    after "2" insert -- -oxazoline--.

Signed and Sealed this

Fourteenth Day of December, 1993

Attest:

BRUCE LEHMAN

Attesting Officer    Commissioner of Patents and Trademarks